(12) United States Patent
Rosborough et al.

(10) Patent No.: US 6,263,241 B1
(45) Date of Patent: Jul. 17, 2001

(54) METHOD AND APPARATUS FOR TREATMENT OF CARDIAC ELECTROMECHANICAL DISSOCIATION

(75) Inventors: John P. Rosborough, Houston; D. Curtis Deno, Missouri City, both of TX (US)

(73) Assignee: Intermedics, Inc., Angleton, TX (US)

(*) Notice: Subject to any disclaimer, the term of this patent is extended or adjusted under 35 U.S.C. 154(b) by 0 days.

(21) Appl. No.: 09/303,380

(22) Filed: Apr. 30, 1999

(51) Int. Cl.[7] ........................................... A61N 1/39
(52) U.S. Cl. ................................................ 607/6
(58) Field of Search .......................... 607/4, 6, 17, 23, 607/24, 5

(56) References Cited

U.S. PATENT DOCUMENTS

| | | | |
|---|---|---|---|
| 3,815,611 | * 6/1974 | Denniston, III | 607/17 |
| 4,303,075 | * 12/1981 | Heilman et al. | 607/23 |
| 4,404,972 | 9/1983 | Gordon et al. | 128/419 PG |
| 4,800,883 | 1/1989 | Winstrom | 128/419 D |
| 4,880,005 | 11/1989 | Pless et al. | 128/419 PG |
| 4,904,472 | 2/1990 | Belardinelli et al. | 514/263 |
| 4,980,379 | 12/1990 | Belardinelli et al. | 514/821 |
| 5,002,052 | 3/1991 | Haluska | 128/419 PG |

(List continued on next page.)

OTHER PUBLICATIONS

*Advanced Cardiac Life Support*, published by American Heart Association, pp. 1–10 to 1–28, 17–1 to 17–10 (1997).
Bocka, J.J., et al., "Electromechanical Dissociation in Human Beings: An Echocardiographic Evaluation", *Annals of Emergency Medicine*, 17 (5), pp. 450–452, (May 1988).
Cripps, T., et al., "The Management of Electromechanical Dissociation", *Resuscitation*, 22 (2), pp. 173–180, (1991).
Grubman, E.M., et al., "Cardiac Death and Stored Electrograms in Patients With Third–Generation Implantable Cardioverter–Defibrillators", *Journal of the American College of Cardiology*, 32 (4), pp. 1056–1062, (Oct. 1998).

Primary Examiner—William E. Kamm
(74) Attorney, Agent, or Firm—Schwegman, Lundberg, Woessner & Kluth, P.A.

(57) ABSTRACT

An apparatus and method for treating post-defibrillation electromechanical dissociation ("EMD"). A first embodiment comprises an implantable defibrillator, which may include cardioversion and pacemaker capabilities, which has the capability of detecting and treating post defibrillation EMD. The stimulator/defibrillator has one or more leads with electrodes. At least one electrode for defibrillation may be an endocardial or epicardial electrode or other suitable defibrillation electrode. A sense circuit senses the electrical condition of the heart of the patient. A hemodynamic sensor senses a parameter correlated to the state of blood flow. The cardiac stimulator/defibrillator detects ventricular tachyarrhythmia including fibrillation and terminates ventricular tachyarrhythmia. After termination of the ventricular tachyarrhythmia, the stimulator/defibrillator can detect the presence of electrical rhythm in the heart correlated, however, with inadequate blood flow to sustain life. Under such conditions, the device provides an output to stimulate the heart to overcome electromechanical dissociation and restore adequate blood flow. The device may also be an external therapy device, as part of, or in conjunction with an external defibrillator. The method for treating the heart to restore blood flow where electromechanical dissociation occurs after termination of a ventricular tachyarrhythmia or ventricular fibrillation comprises identifying electromechanical disassociation after termination of a ventricular tachyarrhythmia or a fibrillation and providing electrical therapy, the therapy comprising a series of packets of electrical pulses.

19 Claims, 9 Drawing Sheets

U.S. PATENT DOCUMENTS

| | | |
|---|---|---|
| 5,179,946 | 1/1993 | Weiss .................................. 128/419 D |
| 5,183,040 | 2/1993 | Nappholz et al. ............. 128/419 PG |
| 5,215,083 | 6/1993 | Drane et al. ...................... 128/419 D |
| 5,305,745 | 4/1994 | Zacouto ................................ 128/637 |
| 5,383,912 | 1/1995 | Cox et al. ............................... 607/32 |
| 5,405,362 | 4/1995 | Kramer et al. ............................ 607/5 |
| 5,476,484 * | 12/1995 | Hedberg ................................. 607/24 |
| 5,480,412 | 1/1996 | Mouchawar et al. ..................... 607/6 |
| 5,480,413 | 1/1996 | Greenhut et al. ....................... 607/14 |
| 5,496,361 | 3/1996 | Moberg et al. ....................... 607/122 |
| 5,628,777 | 5/1997 | Moberg et al. ....................... 607/122 |
| 5,713,935 | 2/1998 | Prutchi et al. .......................... 607/28 |
| 5,782,879 | 7/1998 | Rosborough et al. ................... 607/6 |
| 5,782,883 | 7/1998 | Kroll et al. ............................. 607/14 |
| 5,792,183 | 8/1998 | Esler ......................................... 607/4 |
| 5,799,350 | 9/1998 | Ferek-Petric et al. ................. 607/17 |
| 5,935,158 | 8/1999 | Holmstrom et al. ................. 607/116 |
| 5,999,850 | 12/1999 | Dawson et al. ........................... 607/4 |
| 6,009,349 * | 12/1999 | Mouchawar et al. ..................... 607/6 |
| 6,057,137 | 5/2000 | Tranquillo et al. .................. 435/174 |

* cited by examiner

METHOD AND APPARATUS FOR TREATMENT OF CARDIAC ELECTROMECHANICAL DISSOCIATION

FIELD OF OUR INVENTION

Our invention is directed towards a method for treating cardiac dysfunction arising from post-defibrillation electromechanical dissociation, and to an apparatus for providing such treatment. In particular, the invention relates to an implantable cardiac cardioverter-defibrillator, capable of detecting fibrillation, delivering a defibrillating shock, sensing electrical cardiac rhythmicity coupled with inadequate blood flow and delivering a therapy to restore cardiac function.

BACKGROUND OF OUR INVENTION

Electromechanical dissociation (EMD) is a clinical condition of cardiac arrest with no palpable pulse or blood flow although coordinated ventricular electrical activity exists. This does not exclude the possibility of very weak ventricular contractions, not usually perceptible by standard external or indirect clinical means, which do not produce significant perfusion pressure capable of sustaining life. EMD may occur as the primary modality of cardiac arrest, distinct from fibrillation. Where EMD occurs, the prognosis for recovery is very poor, with survival rates reported on the order of a few percent. When persistent and untreated, EMD is associated with global ischaemia, which will result in rapidly progressive and irreversible brain damage within minutes.

EMD also commonly occurs after defibrillation. In the past, the accepted remedy has been to provide continued life-support while waiting for cardiac output to return. Life support measures commonly include CPR and the administration of drugs such as epinephrine in connection with a search for and removal of reversible causes for the condition. Chest compressions and ventilation may extend the period of viability, although it is well known that standard CPR is a poor substitute for cardiac contractions. If cardiac output does not spontaneously return death is probable. This may particularly be the case for patients with implantable automatic cardioverter-defibrillators. The device may terminate an episode of ventricular fibrillation, cardiac electrical rhythm may be restored, and the patient may nevertheless die as a result of EMD.

The basic implantable cardioverter/defibrillator system consists of at least one electrode attached to the heart and connected by a flexible lead to a shock or pulse generator. This generator is a combination of a power source and the microelectronics required for the system to perform its intended function. An implantable cardioverter/defibrillator may also include a pacemaker to treat bradycardia. Many cardioverter/defibrillators in current use incorporate circuits and antennae to communicate non-invasively with external instruments called programmers. Implantable cardioverters/defibrillators have the capability of correcting dangerous tachyarrhythmias and fibrillation by applying selected stimulation patterns or high-energy shocks. High-energy shocks are used primarily to correct life-threatening tachyarrhythmias by essentially stopping the heart and allowing an appropriate rhythm to re-establish itself.

There remains a need, however, for apparatus that can not only terminate fibrillation, but can also identify post-defibrillation electromechanical dissociation, and provide a therapy.

It is an object of our invention, therefore, to provide a method for treating post-defibrillation electromechanical dissociation.

It is also an important object of our invention to provide an apparatus that can stimulate the heart in the presence of post-defibrillation EMD in such a manner as to restore life-sustaining cardiac output.

Another important object of our invention is to provide an implantable cardioverter-defibrillator with apparatus for sensing and treating post-defibrillation EMD.

SUMMARY OF OUR INVENTION

We have invented an implantable defibrillator, which may include cardioversion and pace maker capabilities, which has the capability of detecting and treating post defibrillation EMD. The implantable defibrillator of our invention comprises a power source and microelectronic apparatus in a hermetically sealed case, and means for detecting and treating EMD.

The stimulator/defibrillator may be connected to the heart by one or more leads, the leads bearing electrodes. At least one electrode serves as an indifferent electrode, which electrode may be part of the hermetically sealed case. At least one electrode for defibrillation is also provided. This electrode may be an endocardial or epicardial electrode or other suitable defibrillation electrode, as is known in the art. A sense circuit senses the electrical condition of the heart of the patient. A hemodynamic sensor is also provided for sensing a parameter correlated to the state of blood flow. The cardiac stimulator/defibrillator is capable of detecting ventricular tachyarrhythmia including fibrillation and providing a therapy to terminate ventricular tachyarrhythmia. After termination of the ventricular tachyarrhythmia, the stimulator/defibrillator can detect the presence of electrical rhythm in the heart correlated, however, with inadequate blood flow to sustain life (i.e., EMD). Under such conditions, the device provides an output to stimulate the heart to overcome electromechanical dissociation and restore adequate blood flow.

The device of our invention may also be used as an external therapy device, as part of, or in conjunction with an external defibrillator. We have also invented a method for treating the heart to restore blood flow where electromechanical dissociation occurs after termination of a ventricular tacyarrhythmia or ventricular fibrillation. The method comprises identifying electromechanical dissociation after termination of a ventricular tach arrhythmia or a fibrillation and providing electrical therapy, the therapy comprising a series of packets of electrical pulses.

We will now describe our preferred embodiment of our invention, in connection with the accompanying drawings.

DESCRIPTION OF OUR PREFERRED EMBODIMENT

Figure 1:
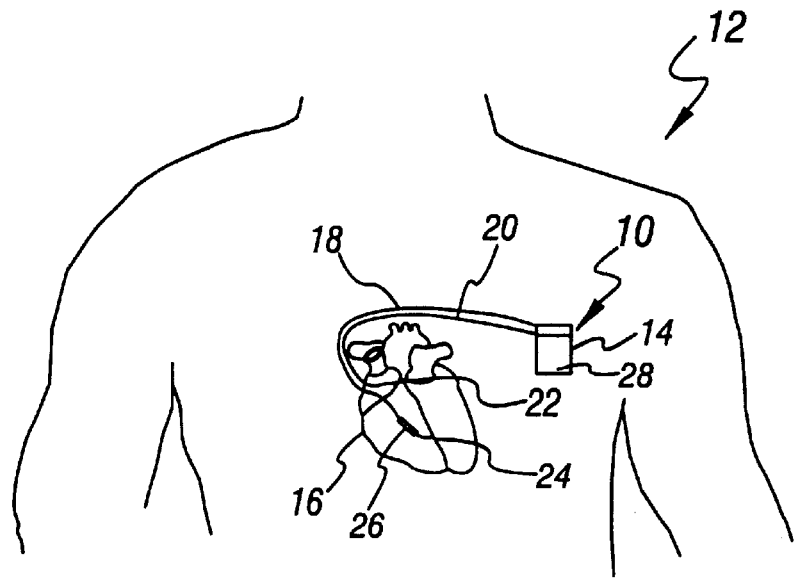
FIG. 1 is an illustration of an implantable pacemaker/defibrillator connected to the heart of the patient.

We will now describe the preferred embodiments of the present invention in connection with the accompanying drawings. In the drawings like numerals are used to indicate like parts throughout.

FIG. 1 represents an implantable cardiac defibrillator 10 in accordance with our invention implanted in the body of a patient 12. The stimulator defibrillator 10 comprises a hermetically sealed can 14 containing electronic components and electrically connected to the heart 16 by a plurality of leads 18, 20. The leads 18, 20 have electrodes 22, 24, as is known in the art, for both stimulating and sensing the heart. A defibrillation electrode 26 is also provided. The defibrillation electrode 26 is illustrated as an endocardial electrode, but epicardial patch electrodes and other forms of defibrillation electrodes are known in the art and could be used. An indifferent electrode 28 should also be provided. The indifferent electrode 28 may be a portion of the medically sealed case 14, or may be a separate electrode. For example, electrodes provided for so-called "bipolar" or "unipolar" pacing may be used as indifferent electrodes on the leads 18, 20 as a matter of design choice. Transvenous electrodes situated in, for example, the coronary venous system, such as posterior cardiac veins, may also be used.

Figure 2:
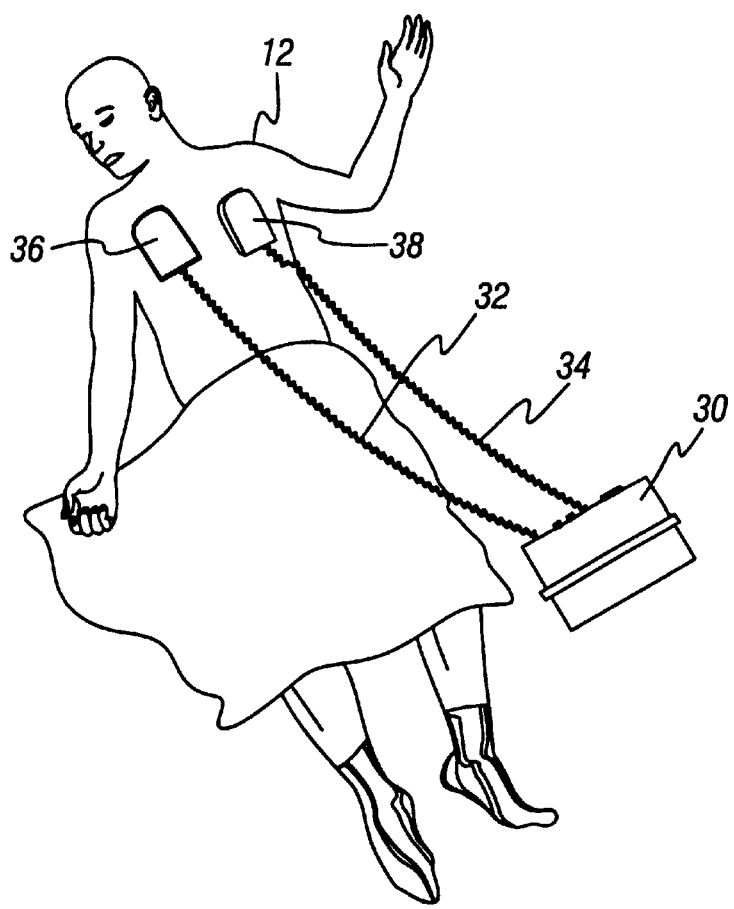
FIG. 2 is an illustration of an external stimulator connected to a patient.

The stimulator/defibrillator of our invention may also be used as an external device as illustrated in FIG. 2. In FIG. 2, an external apparatus is illustrated connected to the patient 12 by leads 32, 34 and pad or patch electrodes 36, 38. Many configurations of suitable electrodes are known to those skilled in the art. Transcutaneous electrodes, as illustrated, may be employed, but subcutaneous electrodes, endoesophageal electrodes, or electrodes placed on the tongue or in the oral cavity or on the thorax or abdomen have also been suggested. Any suitable electrode configuration could be deployed with our invention.

Figure 3:
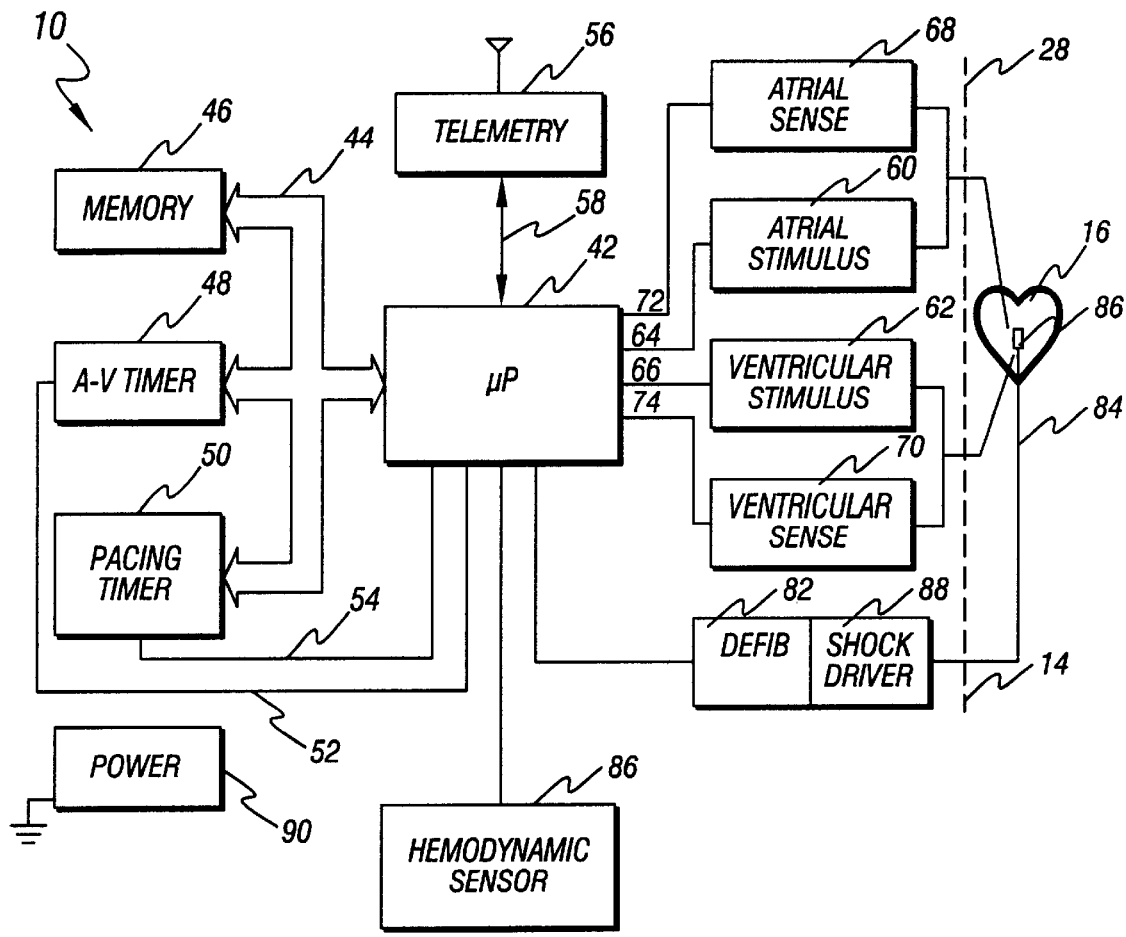
FIG. 3 is a block diagram of an implantable pacemaker/defibrillator.

FIG. 3 is a block diagram illustrating the pacemaker/defibrillator 10 according to our invention. A microprocessor 42 preferably provides pacemaker control and computational facilities. It will be appreciated that other forms of circuitry, such as analog or discrete digital circuitry, can be used in place of microprocessor 42. However, a microprocessor is preferred for its miniature size and its flexibility, both of which are of critical importance in the implantable systems in which it is envisioned the invention will find use. A particularly energy efficient microprocessor which is designed specifically for use with implantable medical devices is fully described in Gordon, et al., U.S. Pat. No. 4,404,972, which is also assigned to our assignee and the disclosure thereof is incorporated herein by reference.

The microprocessor 42 has inputoutput ports connected in a conventional manner via bi-directional bus 44 to a memory 46, an A-V interval timer 48, and a pacing interval timer 50. In addition, the A-V interval timer 48 and pacing interval timer 50 each has an output connected individually to a corresponding input port of the microprocessor 42 by lines 52 and 54 respectively.

Memory 46 preferably includes both ROM and RAM. The microprocessor 42 may also contain additional ROM and RAM as described in the Gordon, et al. U.S. Pat. No. 4,404,972. The pacemaker operating routine is stored in ROM. The RAM stores various programmable parameters and variables.

The A-V and pacing interval timers 48 and 50 may be external to the microprocessor 42, as illustrated, or internal thereto, as described in the Gordon, et al. U.S. Pat. No. 4,404,972. The timers 48, 50 are suitable conventional up or down counters of the type that are initially loaded with a count value and count up to or down from the value and output a roll-over bit upon completing the programmed count. The initial count value is loaded into the timers 48, 50 on bus 44 and the respective roll-over bits are output to the microprocessor 42 on lines 52, 54.

The microprocessor 42 preferably also has an input/output port connected to a telemetry interface 56 by line 58. The defibrillator, when implanted, is thus able to receive pacing, arrhythmia therapy, and rate control parameters from an external programmer and send data to an external receiver if desired. Many suitable telemetry systems are known to those skilled in the art. One such system and encoding arrangement is described in Armstrong et al., U.S. Pat. No. 5,383,912 which is also assigned to our assignee. That description is incorporated herein by reference.

The microprocessor output ports are connected to inputs of an atrial stimulus pulse generator 60 and a ventricle stimulus pulse generator 62 by control lines 64 and 66 respectively. The microprocessor 42 transmits pulse parameter data, such as amplitude and width, as well as enable/disable and pulse initiation codes to the generators 60, 62 on the respective control lines. The microprocessor 42 also has input ports connected to outputs of an atrial sense amplifier 68 and a ventricular sense amplifier 70 by lines 72 and 74 respectively. The atrial and ventricular sense amplifiers 68, 70 detect electrical conditions in the heart including fibrillation and occurrences of P-waves and R-waves. The atrial sense amplifier 68 outputs a signal on line 72 to the microprocessor 42 when it detects a P-wave. The ventricular sense amplifier 70 outputs a signal on line 74 to the microprocessor 42 when it detects an R-wave.

The implantable cardiac stimulator 10 also has a defibrillator circuit 82. If fibrillation is detected either through the atrial or ventricular sense amplifiers 68, 70 or as a consequence of anti-tachycardia therapy, a high-energy shock can be delivered through defibrillation lead 84 and electrode 86. An electric circuit through the heart is completed through the indifferent electrode 28, represented here as part of the can 14.

Detection algorithms for detection of tachycardias and fibrillation are described in Pless, et al., U.S. Pat. No. 4,880,005, incorporated herein by reference. Although an endocardial electrode and use of the conductive part of the can or case are suggested by the drawing, patch-type epicardial electrodes for defibrillation are also known. The shock is controlled by a shock driver circuit 88, which will be more particularly described hereafter.

A hemodynamic sensor 86 is connected to the microprocessor 42. The hemodynamic sensor 86 detects a parameter of body correlated to blood flow. Numerous types of hemodynamic sensors have been suggested. Impedance sensing has been used to detect the cardiac output of the heart. Pressure sensors, flow meters, Doppler flow sensors, ion transport sensors, oxygen, pH, piezoelectric and acoustic (acceleration or heart sound) sensors, among others, have been suggested, all of which detect parameters which can be correlated, more or less directly, to blood flow. For purposes of our invention, it is important to have a sensor, such as the ventricular sense amplifier 70, capable of detecting the electrical condition of the heart and a second independent sensor, such as the hemodynamic sensor 86, capable of detecting a physiological parameter correlated to blood flow.

All of the aforementioned components are powered by a power supply 90. The power supply 90 may comprise either standard or rechargeable batteries or both, which may be dedicated to the operation of different parts of the stimulator 10.

Figure 4:
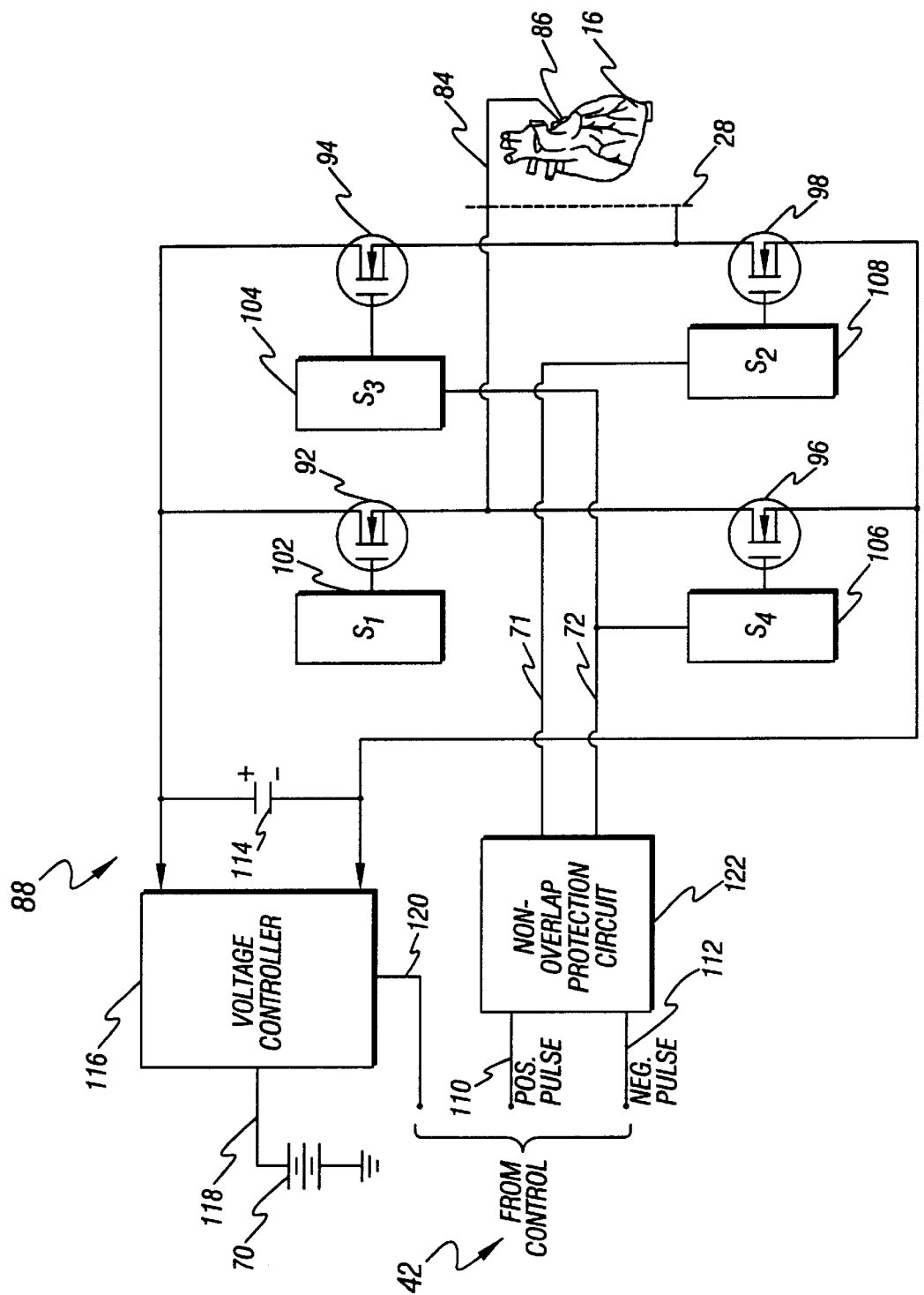
FIG. 4 is a block diagram of an output circuit for use in the defibrillator of FIG. 3.

In the preferred embodiment of our invention, we consider it desirable to produce multi-phasic shocks for defibrillation through the shock driver 88. Circuitry particularly well adapted for producing such waveforms is described in detail in U.S. Pat. No. 4,800,883 to Winstrom, the disclosure of which is incorporated herein by reference. Circuitry for the shock driver 88 is shown with greater particularity in FIG. 4. FIG. 4 illustrates the shock driver 88 connected to the patient's heart 16 through the lead 84 and electrode 86 and through the indifferent electrode 28. To produce a biphasic waveform, a bank of four three-terminal semiconductor switches 92, 94, 96, 98, such as insulated gate bipolar transistor (IGBT) switches, may be employed. It will be understood, however, that our invention can be employed with monophasic pulse generators and with pulse generators incorporating multiphasic stimulation. The switches 92, 94, 96, 98 are controlled by drivers 102, 104, 106, 108 respectively. The drivers 102, 104, 106, 108 are controlled by command pulses from the microprocessor 42 through control lines 110 and 112, as will be more particularly described below. The energy to produce biphasic defibrillating shocks is supplied from high voltage capacitor 114. High voltage capacitor 114 is connected to switches 92 and 94, and current therefrom returns via switches 96 or 98. The lead 84 is connected between switches 92 and 96 while the indifferent electrode 28 is connected between switches 94 and 98.

The amount of energy delivered to the heart is dependent upon the voltage on the high voltage capacitor. The voltage appearing on the capacitor 114 is controlled by voltage controller 116, which is connected to a source of power such as the battery or power supply 70 through line 118. The voltage controller 116 is controlled through a line 120 from the microprocessor 42. This configuration is described in more detail in the Winstrom patent mentioned above. In the configuration shown, to produce a unidirectional current pulse through the heart 16, the microprocessor 42 issues a command through a nonoverlap protection circuit 122 to drivers 102 and 108, closing switches 92 and 98. Both before and after the command, all switches are normally opened. To produce an opposite current, the microprocessor 42 issues a command on line 124 to drivers 104 and 106, closing switches 94 and 96 and directing the current flow in the opposite direction through the heart 16.

Bi-phasic or mono-phasic electrical shocks may be delivered by this apparatus to terminate ventricular fibrillation. In addition, cardioverting therapies of lower voltage are known and applied to terminate ventricular tachyarrhythmias. See, for example, Pless, et al. U.S. Pat. No. 4,880,005 and Haluska, U.S. Pat. No. 5,002,052. Although cardioverting shocks may terminate the ventricular tachyarrhythmia, cardiac output is not restored in some patients, even though a recognizable and apparently adequate electrocardiogram is detected. This condition is called herein electromechanical dissociation (EMD), implying that the electrical condition of the heart is dissociated with the mechanical or pumping action of the organ. This condition is rapidly fatal if not corrected. We have found that an electrical stimulation therapy applied momentarily after detection of electromechanical dissociation can be effective in restoring cardiac output. This is illustrated in the flow chart of FIG. 5.

Figure 5:
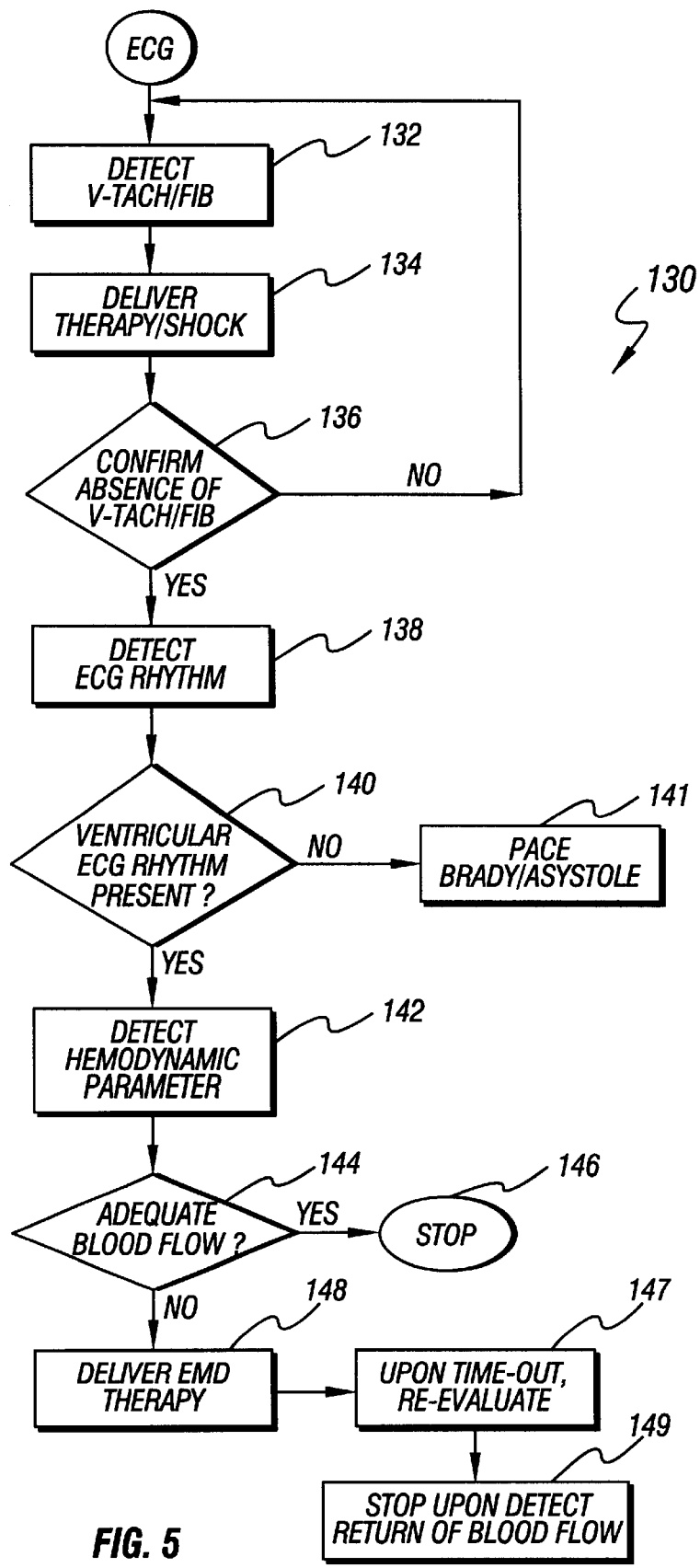
FIG. 5 is a flow chart for representing the therapy according to our invention.

FIG. 5 illustrates an algorithm 130 for the termination of electromechanical dissociation following termination of a ventricular tachyarrhythmia including fibrillation. According to the algorithm 130, the stimulator/defibrillator 10 detects ventricular tachyarrhythmia or fibrillation 132 and delivers a therapy or shock 134. After delivery of the therapy, the absence of ventricular tachyarrhythmia or fibrillation is confirmed 136. The device then senses the ECG 138 through the appropriate ventricular or ventricular sense amplifier 62 or a similar device. If the ECG is not present 140, pacing therapy for bradycardia or asystole may be applied 141. This therapy may be adjusted in accordance with known principles. See, e.g., Haluska, '052. If, on the other hand, the ECG is present, the device 10 will attempt to detect the hemodynamic parameter 142 through the hemodynamic sensor 86. If adequate blood flow is detected 144, the functioning of the heart has been restored and the algorithm can stop 146. If adequate blood flow is not detected, however, an EMD therapy 148 must be applied. After a selected period of time, the device should re-evaluate 147 the patient's condition. If the patient is improving slowly or not at all, the EMD therapy may be restarted. Other therapies may also be used. If return of blood flow is detected 149, the therapy may be stopped.

Figure 6:
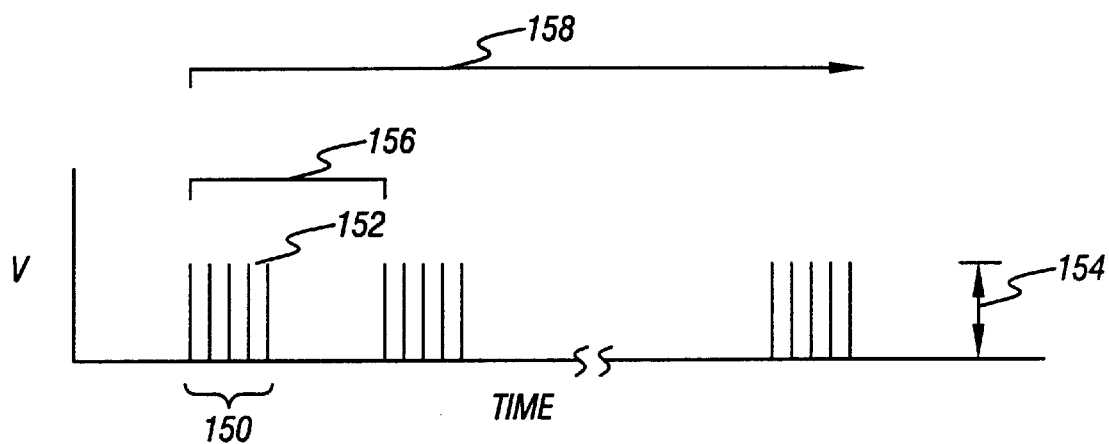
FIG. 6 is timing diagram for the therapy of our invention.

We have discovered that, following termination of a ventricular tachyarrhythmia or fibrillation, EMD can be treated by a therapy comprised of a series of packets of electrical pulses, the pulses being from about 20 to about 400 microseconds in length and having a frequency of from 20 Hz to about 500 Hz and an amplitude from about 20 volts to about 80 volts. The packets should be comprised of about 1 to 40 pulses and leading pulses of adjacent packets should be separated from each other by intervals from about 0.1 seconds to about 2 seconds. The entire series should last at least 2 seconds. This is illustrated in FIG. 6, which shows a time by voltage amplitude graph. Packets 150 of electrical pulses 152 are shown. These pulses should have an amplitude 154 from about 20 volts to about 80 volts in the implanted device. Each packet should be comprised of between 1 to 20 pulses and should be separated by intervals 156 of about 0.1 seconds to about 2 seconds. The duration 158 of the series of packets should be at least 2 seconds.

Figure 7:
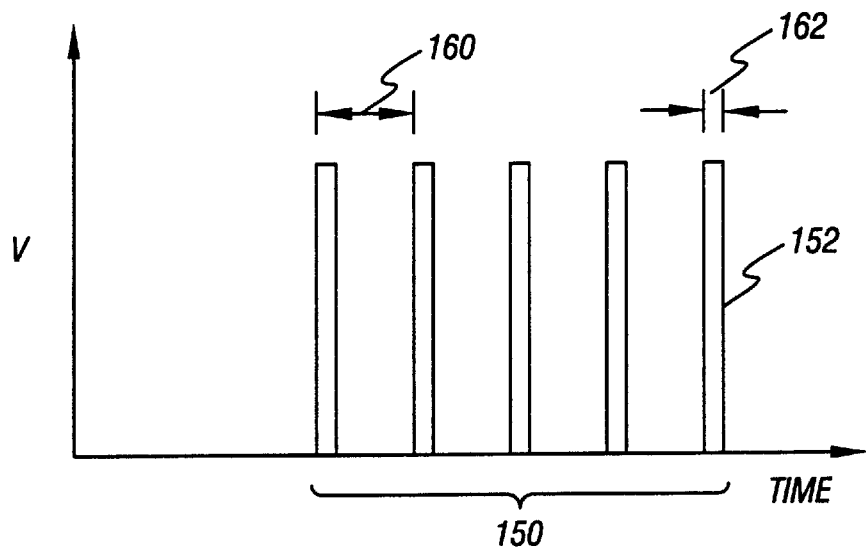
FIG. 7 is an enlarged portion of the timing diagram of FIG. 6.

The fine structure of the packets is further illustrated in FIG. 7. We have found that the pulses 152 should have a frequency 160 from about 50 Hz to about 100 Hz determined from a similar feature, for example, the leading edge of one pulse to the similar feature of the following pulse. The pulses 152 should have a length 162 from about 150 milliseconds to about 250 milliseconds, most preferably about 200 milliseconds.

We have found that the pulses should most preferably have an amplitude of between 20 volts and 60 volts and that the leading pulses in adjacent packets should be separated from each other by intervals of about 0.5 seconds. Moreover, the therapy appears to be more effective when the packets are comprised of about 20 pulses or less. In the implantable device, a voltage level of about 20 volts appears to be effective. In an external device a higher applied voltage would be necessary in order to have a voltage drop across the heart which effectively reaches 20 volts.

Figure 9:
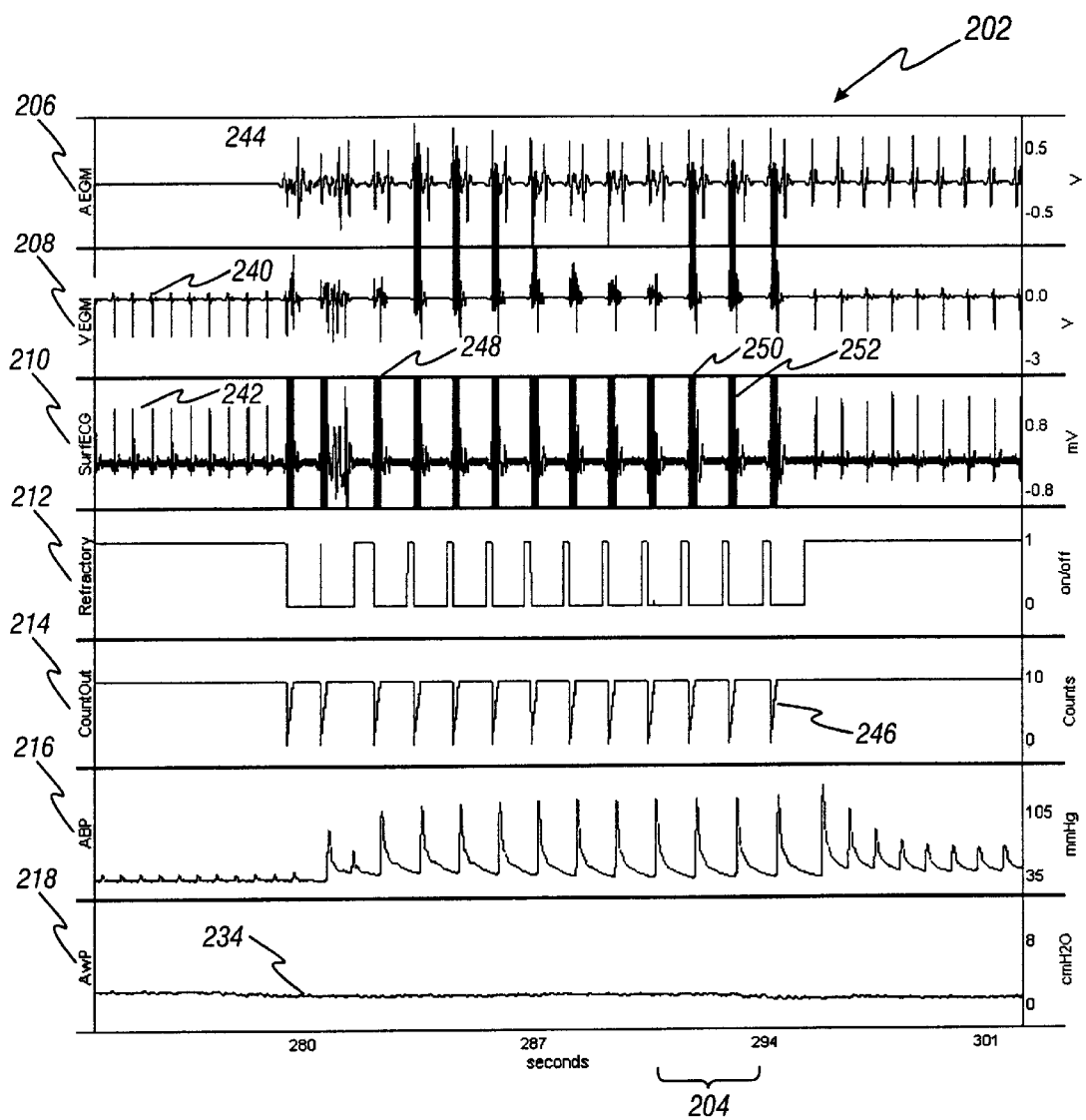
FIG. 9 is an enlarged segment of the graph of FIG. 8.
Figure 10:
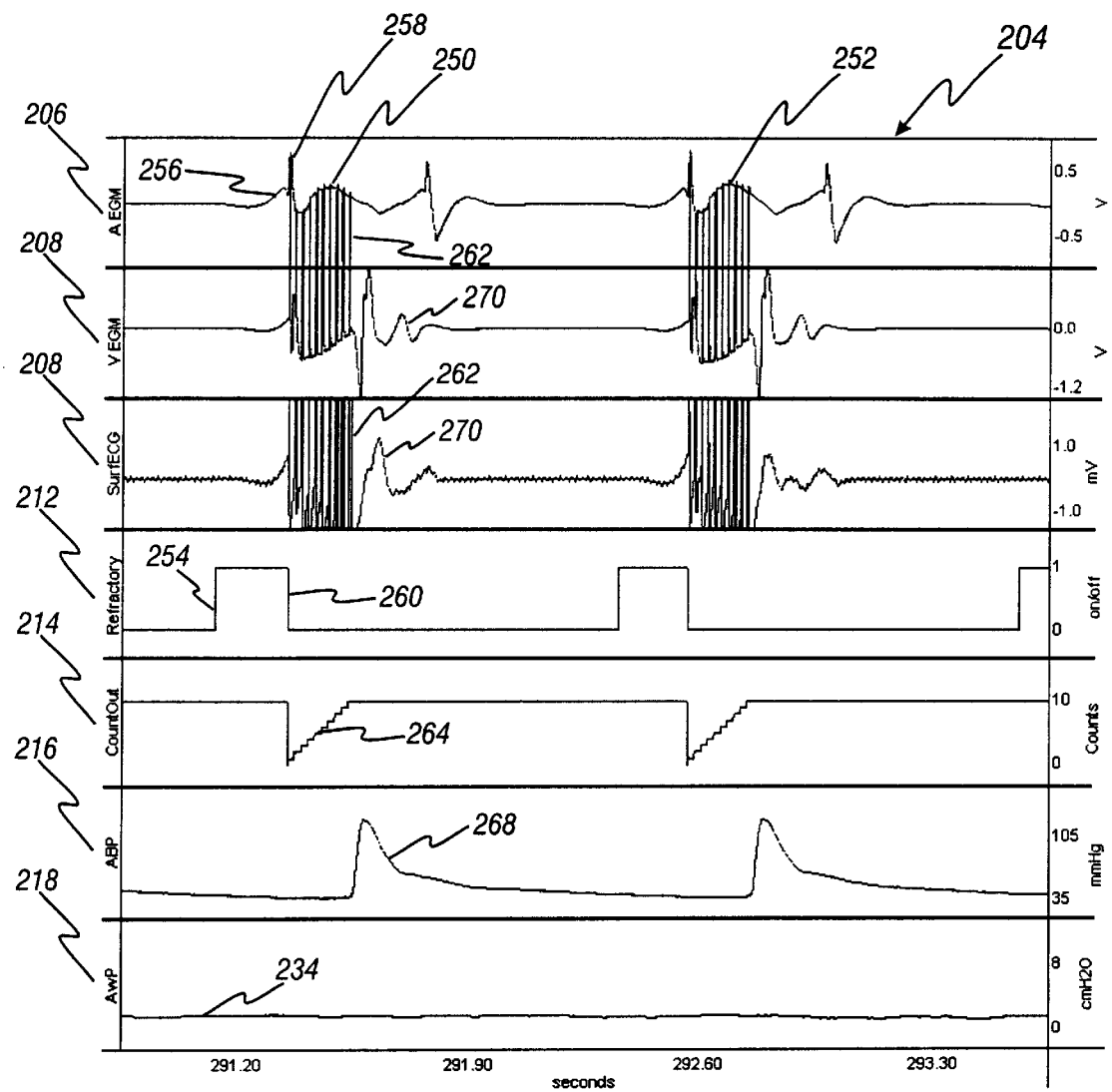
FIG. 10 is a further enlarged segment of the graphs of FIG. 8 and FIG. 9.

We will now describe an exemplary application of our therapy. In connection with the development of our invention, we have investigated the effectiveness of the therapy in a canine model. An exemplary incidence, taken from our study No. ST012099, is illustrated in FIGS. 8, 9, and 10.

Figure 11:
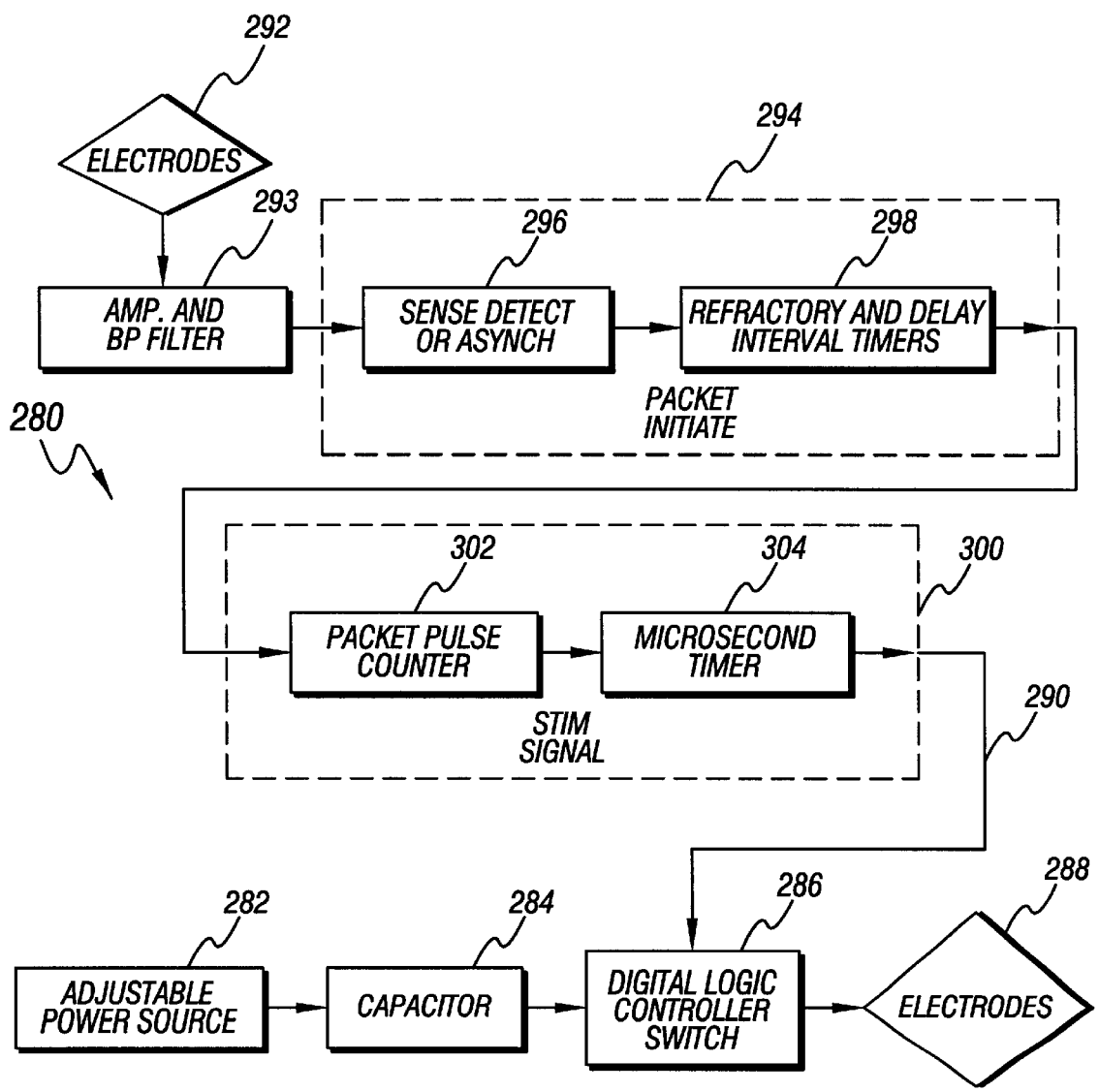
FIG. 11 is a block diagram of an external apparatus for use in our invention.

FIG. 11 illustrates, in block diagram, an external device used to produce and investigate the effectiveness of the therapy described herein. The external device 280 comprises an adjustable power source 282 which supplies electrical power to a capacitor or capacitor bank 284. Energy stored in capacitor bank 284 is passed through a digital logic controlled pulse switch 286 to electrodes 288. For purposes of study ST012099 testing, subcutaneous patch electrodes were employed, but many different electrode configurations could be used including surface electrodes or electrodes placed within the body cavities, within the venous system, or within the heart itself.

In the external apparatus 280, a signal is produced on line 290 to control the digital logic controlled pulse switch 286. The signal on line 290 may be initiated at an asynchronous rate or in response to sensed signals detected through EGM detection electrodes 292 and band pass filter 293. As with the electrodes which deliver therapy (which could be the same as the EGM detection electrodes), numerous different electrode configurations are known and could be employed to detect the EGM signal. A packet initiate block 294 begins the process of initiating the therapy by receiving the EGM signal in a sense circuit 296, if it is desired to synchronize the therapy to a feature of the detected EGM signal. When the selected feature or level of EGM is detected, a refractory interval timer 298 times out for a preselected period from the feature before permitting a subsequent detection. Also, after a selected delay, a simulation signal block 300 produces a set of control signals to initiate therapy. The stimulation signal block 300 comprises a packet pulse counter 302 which triggers a predetermined number of pulses within a packet of the therapy. A microsecond timer 304 controls the duration of pulses. The resulting control signal on line 290 controls the digital logic control switch 286 to produce the desired therapy at the electrodes 288. That therapy and its results will now be discussed in connection with FIGS. 8, 9 and 10.

Figure 8:
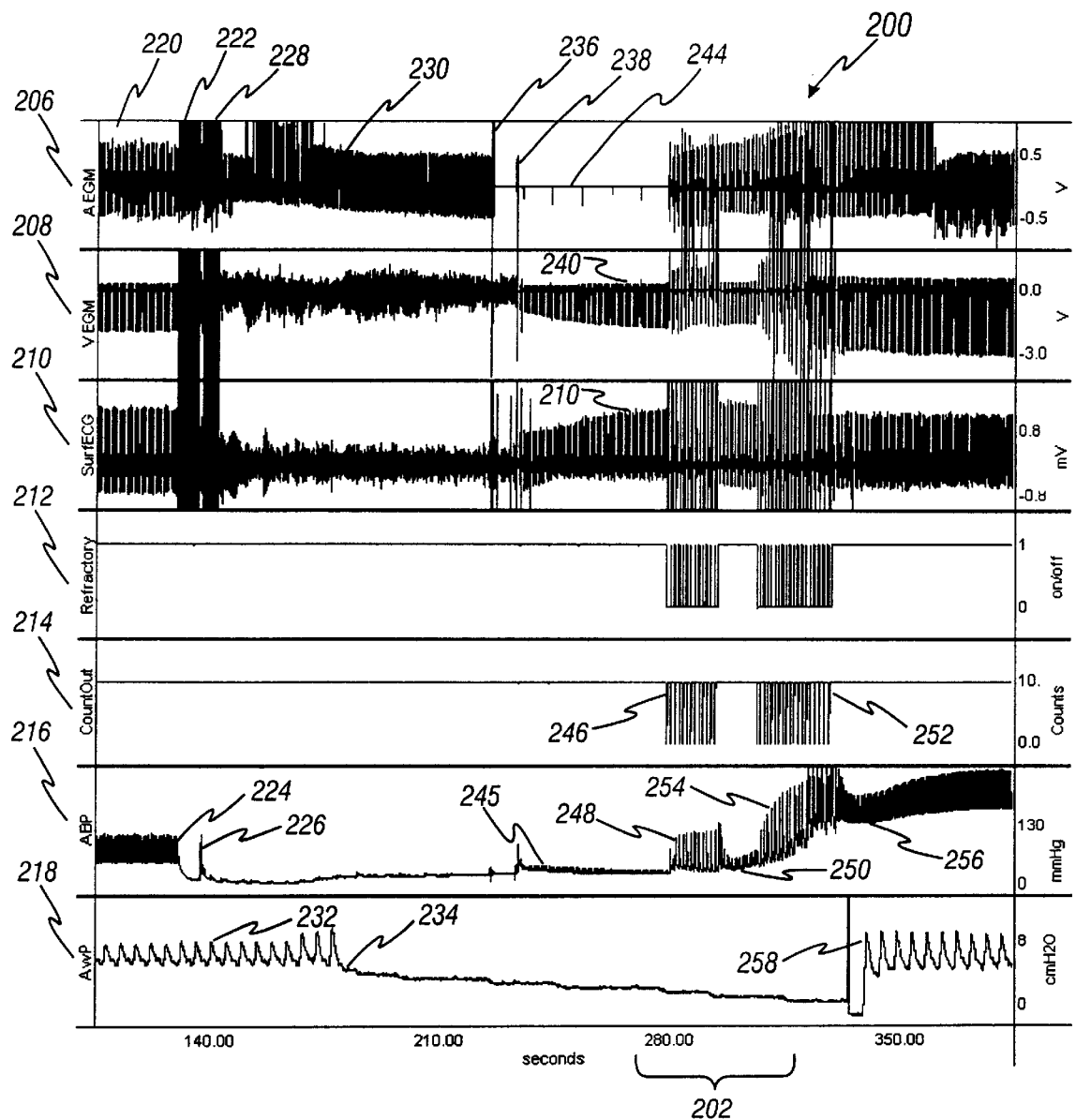
FIG. 8 is a graph of an application of our invention in an animal (canine) model.

FIG. 8 is an illustration 200 of data recorded during an instance of induced fibrillation terminated by a defibrillation shock and followed by EMD. FIG. 9 is an expanded view of a portion 202 of the graph of FIG. 8. Similarly, FIG. 10 is an expanded portion 204 of the graph of FIG. 9. In FIG. 8, the bracket labeled 202 identifies the segment expanded in FIG. 9. In FIG. 9, the bracket labeled 204 identify the segment expanded in FIG. 10. Each of the FIGS. 8, 9 and 10 give similar information. The top line 206 of the figures represents an amplified atrial electrogram on a scale of time against volts. The second line 208 represents the amplified ventricular electrogram on the same scale. The third line 210 represents the surface electrocardiogram on a scale of time versus millivolts.

The fourth line 212 represents the refractory status of the sense amplifiers of the automatic device used to apply the therapy. It is significant because it enables one to determine when the automatic device has sensed a particular feature of the electrogram, for example in the atrium, and has begun to apply the therapy. It will be explained in greater detail in connection with FIG. 10. A state of one or "high" indicates that the sense amplifier is operational. A state of zero, or "low", indicates that the sense amplifier has been turned off for a preselected period of time. In this case, the sense amplifiers are turned off to allow therapy to be applied without effecting the sense circuits.

The fifth line 214 is a counter counting the application of packets of electrical pulses. This can also be seen most clearly in FIG. 10, and will be explained in greater detail in connection with that figure.

The sixth line 216 is a graph of the arterial blood pressure in millimeters of mercury. The seventh and final line 218 of the figures is a graph of airway pressure and represents the application of a mechanical ventilator.

The therapy illustrated in FIGS. 8, 9 and 10 was applied using an implantable device, but without implantation, the therapy being applied transthoracically across two subcutaneous patch electrodes. A mechanical ventilator was available to assist respiration, if needed. Referring now to FIG. 8, the first period 220 of the graph in FIG. 8, up to about 130 seconds, illustrates normal sinus rhythm. The AEGM 206, VEGM 208 and surface ECG 210 all indicate a normal condition. The refractory line 212 indicates that the sense amplifiers are engaged. As can be seen in the sixth line 216 arterial blood pressure is fluctuating over a systolic to diastolic range in a normal manner. Next AC current 222 was applied to induce ventricular fibrillation. The arterial blood pressure can be seen to be falling 224. However, the first series of AC current cycles 222 was not effective and normal cardiac rhythm and blood pressure 226 resumed spontaneously. A second series of AC current cycles 228 was applied and fibrillation was induced. A fibrillation pattern 230 can be seen extending from about 140 seconds to about 230 seconds. The mechanical ventilator had been used to provide forced breathing, as seen at 232. However, the ventilator was turned off at 234 to more accurately simulate cardiac arrest in an individual outside of the hospital setting, but with either an implanted automatic defibrillator or under care in a non-emergency room setting with an external defibrillator. A first defibrillating shock 236 was applied at about 220 seconds. The first shock was ineffective in terminating the fibrillation and a second shock 238 was delivered. The second shock 238 effectively terminated fibrillation as can be seen at 240 in the ventricular electrogram and 242 in the surface ECG. The sense amplifier of the atrial electrogram, however, was apparently temporarily saturated and no signal was received during this period at 244. Despite the return of an effective and apparently rhythmic electrical waveform in the heart, the arterial blood pressure remained too low 245 to sustain life. This is the classic example of EMD after an electrically terminated fibrillation.

After the condition of EMD had been established for a short period of time, on the order of one minute, the therapy according to our invention was applied at 246. As can be seen on the arterial blood pressure line 216, a sharply increased and widely varying blood pressure was observed at 248. After the imposition of the therapy, blood pressure remained more varied and was beginning to rise at 250. To accelerate improvement, however, a second series of packets was applied at 252. The arterial blood pressure 216 rose sharply 254 and reestablished a regular pattern 256 after the therapy was stopped. The ventilator was again turned on, as indicated at 258.

Application of the therapies can be seen in greater clarity in FIG. 9 which illustrates in expanded scale the first therapy 246. In FIG. 9, the relatively normal electrogram can be seen at 240 and 242 on the ventricular EMG channel and the surface ECG channel, respectively. As noted above, the failure of the atrial EGM channel to sense an electrogram at 244 was a function of the saturation of the sense amplifiers. The therapy represents a series of packets of pulses, as described above. In FIG. 9, the individual pulses can not be distinguished, but the packets can be clearly seen at 248, for example, in the surface ECG 210. A sharp rise in the arterial blood pressure 216 can be seen in response to each of the packets of pulses.

FIG. 10 illustrates in greater detail two of the packets of pulses 250, 252. At this time the ventilator was still turned off, as shown by the airway pressure line 218 at 234. In this instance, the application of the therapy was synchronized to a feature of the electrocardiogram. Thus, the refractory line 212 indicates at 254 that the sense amplifiers have been turned on by the signal going high. A rise in the atrial electrogram at 256 was detected by the sense amplifiers and, after the AEGM had reached a predetermined level, therapy was applied at 258. As the therapy was applied, the sense amplifiers were made refractory, indicated by the falling edge 260 of the refractory line 212. A series of ten pulses 262 was delivered which can be seen in each of the AEGM 206, VEGM 208 and surface ECG 210. The count line 214 indicates in step-wise manner at 264 the condition of a counter counting each of these ten pulses in the packet 250. A pressure pulse 268 is produced by the heart in response to the application of the therapy. This pressure pulse 268 1s synchronized with the QRS complex 270 being produced by the heart.

As pointed out above, application of the therapy described herein was sufficient to restore cardiac output after an episode of electromechanical dissociation following defibrillation in the absence of chest compressions, artificial ventilation or drugs.

While a preferred embodiment of our invention has been described above, it will be apparent to those skilled in the art from consideration of the disclosure herein that various modifications could be implemented without departing from the principles of our invention. Accordingly, it is intended that the scope of our invention be limited only by the appended claims.

What is claimed is:

1. An implantable cardiac stimulator/defibrillator comprising
    a hermetically sealed case;
    at least one lead having an electrode thereon, said electrode being electrically connected to said stimulator/defibrillator;
    an indifferent electrode electrically connected to said stimulator/defibrillator;
    a power source in said case;
    a control circuit connected to said power source;
    a sensing circuit capable of sensing the electrical condition of the heart of a patient;
    a hemodynamic sensor capable of sensing a parameter correlated to the state of blood flow;
    a correlation circuit associated with said control circuit capable of correlating a presence of electrical rhythm in the heart with an absence of a selected level of said parameter after an episode of tachyarrythmia; and
    an output circuit responsive to said correlation and control circuits, said output circuit producing an electrical therapy between said electrode and said indifferent electrode, said therapy comprised of a series of packets of electrical pulses,
    said pulses being from about 20 microseconds in length and having a frequency of from 20 Hz to about 500 Hz and an amplitude of from about 20 V to about 80 V and
    said packets being comprised of from 1 to 40 pulses and leading pulses in adjacent packets being separated from each other by intervals of from about 0.1 seconds to about 2 seconds, and
    said series lasting at least 2 seconds.

2. The stimulator/defibrillator of claim 1 wherein said pulses are less than about 400 microseconds in length.

3. The stimulator/defibrillator of claim 1 wherein said pulses have a frequency of from about 50 Hz to about 100 Hz.

4. The stimulator/defibrillator of claim 1 wherein said pulses have an amplitude of from about 20 V to about 60 V.

5. The stimulator/defibrillator of claim 1 wherein said pulses are about 150 milliseconds to about 250 milliseconds in length.

6. The stimulator/defibrillator of claim 5 wherein said packets are about 200 milliseconds in length.

7. The stimulator/defibrillator of claim 1 wherein the leading pulses in said adjacent packets are separated from each other by intervals of about 0.5 seconds.

8. The stimulator/defibrillator of claim 1 wherein said packets are comprised of about 20 pulses or less.

9. The stimulator/defibrillator of claim 1 further comprising means for synchronizing said therapy to a selected feature of the electrical condition of the heart.

10. The stimulator/defibrillator of claim 1 wherein said hemodynamic sensor is an impedance sensor.

11. The stimulator/defibrillator of claim 1 wherein said hemodynamic sensor is a flow sensor.

12. The stimulator/defibrillator of claim 1 wherein said hemodynamic sensor is a pressure sensor.

13. The stimulator/defibrillator of claim 1 wherein said hemodynamic sensor is an accelerometer.

14. The stimulator/defibrillator of claim 1 wherein said hemodynamic sensor is an acoustic sensor.

15. The stimulator/defibrillator of claim 1 wherein the electrode is a defibrillation electrode.

16. The stimulator/defibrillator of claim 15 wherein the defibrillation electrode is an endocardial electrode.

17. The stimulator/defibrillator of claim 15, wherein the indifferent electrode is at least part of the case of the stimulator/defibrillator.

18. The stimulator/defibrillator of claim 15 wherein said indifferent electrode is a lead electrode.

19. The stimulator/defibrillator of claim 1 where commencement of delivery of said therapy is synchronized with said electrical condition of the heart.

* * * * *

UNITED STATES PATENT AND TRADEMARK OFFICE
CERTIFICATE OF CORRECTION

PATENT NO.     : 6,263,241 B1
DATED          : July 17, 2001
INVENTOR(S)    : John P. Rosborough and D. Curtis Deno It is certified that error appears in the above-identified patent and that said Letters Patent is hereby corrected as shown below:

<u>Column 3,</u>
Line 58, delete "inputoutput" and insert -- input/output --, therefor.

Signed and Sealed this

Twenty-third Day of July, 2002

*Attest:*

*Attesting Officer*

JAMES E. ROGAN
*Director of the United States Patent and Trademark Office*